United States Patent [19]

Masini

[11] Patent Number: 4,689,130
[45] Date of Patent: Aug. 25, 1987

[54] CONTINUOUS PRODUCTION OF HIGHER CHLOROALKANES

[75] Inventor: Jean-Jacques Masini, Chaponost, France

[73] Assignee: ATOCHEM, Courbevoie, France

[21] Appl. No.: 727,685

[22] Filed: Apr. 26, 1985

[30] Foreign Application Priority Data

Apr. 27, 1984 [FR] France .................................. 84 06635

[51] Int. Cl.$^4$ .......................... C07B 39/00; B01J 1/10
[52] U.S. Cl. ............................... 204/157.94; 260/694; 570/253; 422/186; 204/157.95
[58] Field of Search ................... 204/157.94; 422/186, 422/234; 260/694

[56] References Cited

U.S. PATENT DOCUMENTS 872,588   12/1907  Stead .................................... 422/234
3,344,197  9/1967  Reiche et al. ........................ 570/253
3,474,018 10/1969  Goeb et al. ...................... 204/157.94
3,528,900  9/1970  Rosenberg et al. ............. 204/157.94

Primary Examiner—John F. Niebling
Assistant Examiner—Ben Hsing
Attorney, Agent, or Firm—Burns, Doane, Swecker & Mathis

[57] ABSTRACT

The higher chloroalkanes, advantageously the higher chloromethanes, are continuously produced from at least one lesser chloroalkane, by (i) continuously introducing chlorine and said at least one lesser chloroalkane into a stream of reaction medium continuously and essentially autogenously recirculating in a loop circuit which comprises an essentially vertical principal reaction zone, (ii) continuously chlorinating said at least one lesser chloroalkane in said essentially vertical principal reaction zone, and (iii) continuously withdrawing higher chloroalkane product from said stream of essentially autogenously recirculating reaction medium.

29 Claims, 1 Drawing Figure

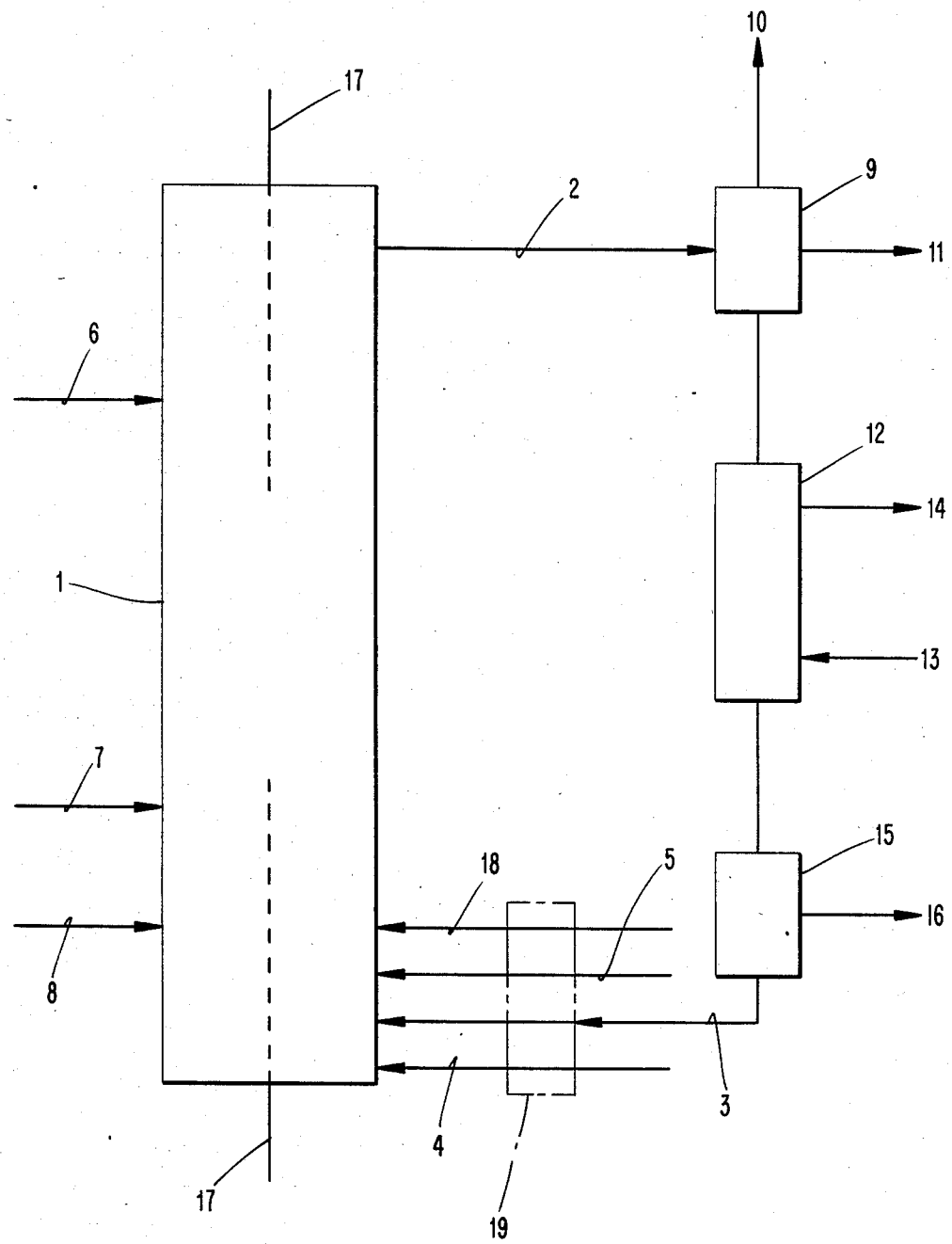

CONTINUOUS PRODUCTION OF HIGHER CHLOROALKANES

BACKGROUND OF THE INVENTION

1. Field of the Invention

The present invention relates to a continuous process for the liquid-phase free-radical chlorination of chlorinated hydrocarbons, and, more especially, to the continuous preparation of the higher chloroalkanes containing 1 or 2 carbon atoms via the liquid-phase free-radical chlorination of one or more chloroalkanes containing a lesser number of chloro substituents per molecule. This invention also relates to certain apparatus useful in carrying out the subject process.

As utilized herein, the expression "chloroalkane(s)" is intended to connote the partially chlorinated hydrocarbon or hydrocarbons used as starting materials in the chlorination reaction according to the invention, and the expression "higher chloroalkane(s)" is intended to connote the final products resulting therefrom.

SUMMARY OF THE INVENTION

Briefly, the present invention features continuously introducing feedstreams of chlorine and chloroalkane starting materials into a circulating reaction medium in the presence of a reaction initiator, controlling the temperature of the reaction medium, and separating the gaseous effluent and the product higher chloroalkane or chloroalkanes from the reaction medium, said process being characterized in that the circulation of the reaction medium is carried out in an open-loop reactor comprising an essentially vertical principal reaction zone, or leg, and said circulation itself being essentially self-established via the differences in hydrostatic pressure existing within the reaction medium.

BRIEF DESCRIPTION OF THE DRAWING

The FIGURE of Drawing is a diagrammatic/schematic representation of exemplary process/apparatus according to the invention.

DETAILED DESCRIPTION OF THE INVENTION

More particularly according to the present invention, the aforementioned differences in hydrostatic pressure principally responsible for establishing circulation of the medium of reaction arise, in particular, from the presence of gaseous hydrochloric acid in said reaction medium as the reaction takes place, and from the differences in the density of the reaction medium, notably because of the increase in the temperature thereof. These phenomena are in and of themselves sufficient to establish and maintain the circulation of the reaction medium within the loop. However, it will be appreciated that it is also within the scope of the invention to initiate the circulation at the beginning of the reaction by means of any suitable pump and/or to operate any such pump during the course of the reaction, whether in addition or supplemental to the aforesaid "natural" circulation.

The subject process can be carried out utilizing either chemical or photochemical initiation. In the case of chemical initiation, the known initiators for chlorination reactions can be used. Exemplary of such chemical initiators, representative are the diazo compounds such as 2,2'-azobisisobutyronitrile or 2,2'-azobis-2,3-dimethylvaleronitrile, or else the peroxy compounds such as lauroyl peroxide and benzoyl peroxide. In general, the compounds can be used neat or in the form of a solution thereof, in particular in a chloroalkane or higher chloroalkane solvent.

The process according to the invention is adopted to provide rates of conversion of chlorine of more than 99%, and even more than 99.5%, using an amount of initiator which typically ranges from $10^{-2}$ to $2.10^{-6}$, and preferably from $5.10^{-3}$ to $10^{-5}$ mole of initiator per mole of chlorine, for initiators having a dissociation constant in toluene of from $5.10^{-7}$ to $5.10^{-3}$ sec$^{-1}$, and preferably from $10^{-6}$ to $2.10^{-4}$ sec$^{-1}$.

In the case of photochemical initiation, a rate of conversion into chlorine of more than 99%, or even more than 99.5%, can be obtained with a luminance ranging from 0.02 to 2 W/cm$^2$ (total electric power of the emitter with reference to the outer surface of the envelope, corresponding to the length of the electric arc of the luminant) and a consumption of electricity corresponding to the photoelectric emission of from 0.1 to 20 W.hr/mole and, more particularly, from 0.5 to 10 W.hr/mole of chlorine used.

In the process according to the invention, the chlorine can be introduced into the reaction loop either in gaseous state or in liquid state.

Depending upon the nature of the chloroalkane or chloroalkanes and the nature of the higher chloroalkane or chloroalkanes sought to be produced, the molar ratio of chlorine to chloroalkane may vary from 0.3/1 to 3/1.

As heretofore mentioned, the process of the invention is characterized in that the reaction is continuously carried out in an open-loop apparatus, the circulation of the reaction medium within said apparatus essentially being established via the differences in hydrostatic pressure prevailing within said reaction medium.

The rate of recirculation of the reaction medium, except for the starting phase, advantageously ranges from 0.05 to 1.5 m/sec, and preferably from 0.10 to 1 m/sec.

The actual operating conditions depend upon a variety of factors, including the type of initiation selected, the length of the principal reaction leg, the temperature and the pressure. In general, the reaction temperature is controlled by use of a cooling or heat exchange fluid, the nature of which, as well as the configuration of the cooling means containing same, being selected to deliver into said principal reaction zone, or leg, a fluid whose temperature advantageously ranges from 20° to 120° C., and preferably from 30° to 90° C. (measurement taken at the base of the reaction leg), the lower values set forth above applying in particular to photochemical initiation. The pressure prevailing within the loop advantageously ranges from 1 to 50 bars, and preferably from 2 to 30 bars.

The process according to the invention is conveniently carried out in the loop apparatus shown diagrammatically in the accompanying FIGURE of Drawing, which apparatus constitutes another embodiment of the invention.

This apparatus comprises a principal reaction zone, or leg 1, which is generally cylindrical and arranged vertically and a circulation loop 2, said reaction zone being charged, essentially at the base thereof, with the reaction medium via the inlet 3, the chlorine via the inlet 4, the chloroalkane(s) via the inlet 5 and, if necessary, an initiator via the inlet 18 in the case of chemical initiation.

The chlorine, the chloroalkane(s) and the initiator, if any, can be introduced separately at the base of the leg 1 or can first be partially premixed (chloroalkane(s), initiator, reaction medium) in a pre-mixer 19.

In the case of chemical initiation, the introduction of initiator can be supplemented along the reaction leg 1 (via the inlets 6 and/or 7), with due consideration being given the length or height of said principal reaction zone, and the length/diameter ratio thereof. Additional reagents can also be introduced into the reaction leg 1 via the inlets 6 and/or 7.

In order to facilitate reaction start-up, hydrochloric acid or an inert gas (for example, nitrogen) can be introduced, if necessary, at the base of the reaction leg via the inlet 8.

The reaction may also be initiated photochemically.

For this purpose, one or more photochemical emitters 17 are disposed within the principal reaction zone.

The apparatus illustrated in the FIGURE of Drawing also comprises, downstream of the principal reaction zone, a separator 9 for separation of the gaseous phase via the outlet 10, said gaseous phase essentially consisting of HCl, alkyl chloride, and unreacted chlorine, from the liquid phase which contains the higher chloroalkanes, and a cooling system 12 including an inlet 13 and outlet 14 for circulating a heat transfer fluid therein. Typically, the outlet (either line 11 or line 16) for the separated liquid phase is located proximate the outlet of the principal reaction leg 1 and comprises the line 11 from the separator 9 in the case of photochemical initiation, but preferably is located downstream of the cooling means 12, via the line 16 comprising the liquid phase separator 15, in the case of chemical initiation. The particular hardware arrangements noted immediately above are well suited for carrying out the process according to the invention, bearing in mind the differences and variations in the principal reaction zone depending upon whether chemical or photochemical is employed, but all such differences/variations remain within the ambit of the invention.

The characteristics and nature of the principal reaction zone 1 essentially depend upon the particular type of initiation selected.

In the case of chemical initiation, and taking into account the fact that in this event the reaction is completely homogeneous, it is particularly advantageous to use a principal reaction leg which permits a long residence or dwell time therewithin. Therefore, preferably selected is a leg or zone whose length/diameter ratio is very high, for example, ranging from 25 to 1000, and preferably from 50 to 250. Purely by way of illustration, the length (or height) advantageously ranges from 1 to 20 m, and more preferably from 2 to 15 m.

In the case of photochemical initiation, and in view of the fact that the reaction is essentially confined to the vicinity of the UV emitters, that is to say, it is no longer homogeneous, it is advisable to multiply the number of UV radiation emitters, which makes it necessary to increase the diameter of the principal reaction zone in order to permit the circulation of the reaction medium. For obvious reasons, disposing the emitters within tubes of great length may present various technological problems. For this reason, and with this particular type of initiation, it is advantageous to select a length/diameter ratio (for the principal reaction leg) ranging from 5 to 100, and preferably from 10 to 50. Also purely by way of illustration, the length (or height) of the principal reaction leg advantageously ranges from 0.1 to 15 m and preferably from 2 to 10 m. It is advantageous to use such number of emitters that the distance between emitters and between the emitters and the sidewall of the reaction zone (in a cross-section perpendicular to the generatrix of the cylinder) ranges from 10 to 250 mm, and preferably from 50 to 200 mm.

The nature and characteristics of the other means and devices comprising the apparatus for carrying out of the process of the invention (means for the introduction of the various reagents, the separation of the gaseous and liquid phases, and for cooling or temperature control) are themselves per se known to this art and are not, individually, embodiments of this invention.

For purposes of simplification, reference has been made in the foregoing description to a single reaction leg (zone). It is clearly apparent, however, that a plurality of such reaction legs having their respective feed inlets 3, 4 and 5, and possibly also 18, 6, 7 and 8, situated parallel to each other, can be connected to the same circulation loop 2, separators 9, 15 and cooling means 12.

The process according to the invention is particularly applicable for the production of the higher chloromethanes, namely, $CH_2Cl_2$, $CHCl_3$ and $CCl_4$ from methylchloride, or from admixtures thereof with chloromethanes having at least one chlorine atom less than the chloromethane or chloromethanes sought to be produced.

This process is also applicable to other chloroalkanes, and in particular to the chloroethanes.

The process of the invention makes it possible to considerably reduce the amount of gas present in the principal reaction zone to limit the content of chlorine in the liquid phase and thus to carry out the reaction essentially completely in liquid phase. The high rate of recirculation makes it possible to obtain a good mixing of the recirculating fluid. This facilitates the intimate admixing of the reagents and the additives. This, in turn, improves all heat exchange, both with regard to the homogenizing of the temperature of the reaction medium and to the removal or dissipation of the heat of reaction.

Finally, in the special case of photochemical initiation, the flow of the fluid advantageously takes place parallel to the axes of the emitters over the greater length thereof. Since, for the remaining length, the angle of incidence is small and the flow occurs over a portion of the emitter which is very close to its point of attachment, the forces exerted by the medium on the emitters are indeed very slight. Furthermore, the dissipation and removal of the electrical energy of an emitter is facilitated by internal recirculation within the reactor itself, which considerably reduces the risk of cracking at the wall, even with emitters of high power (10 kW or even more); it is known, in fact, that too high a wall temperature can give rise to the decomposition of the chloroalkanes, with the formation of deposits on the emitter and concomitant prevention of photoluminous emission.

Too, the process/apparatus of the invention does not require any moving parts, which makes the apparatus assembly particularly simple and considerably limits maintenance expenses and the risk of leakage of reagents, or reaction products, to the external environment.

In order to further illustrate the present invention and the advantages thereof, the following specific examples are given, it being understood that same are intended only as illustrative and in nowise limitative.

EXAMPLE 1

(1) The apparatus employed was as shown in the FIGURE of Drawing, and had the following characteristics:
(i) Dimensions of the cylindrical, principal reaction zone 1:
 (a) length: 1800 mm;
 (b) internal diameter: 85 mm
(ii) Photochemical initiation: UV emitter 17 of an arc length of 1500 mm and a diameter of 38 mm, vertically arranged at the top of the reaction zone, power 65 W;
(iii) Separate inlets 4 and 5 for the reagents at the base of the reaction zone;
(iv) Liquid phase outlet via line 11;
(v) Gaseous phase outlet via line 10;
(vi) Water cooling in a tube exchanger 12.

(2) Within the loop 2 was circulated a mixture comprising, by weight (approximately):
 $CCl_4$: 69%
 $CHCl_3$: 31%
 Traces of HCl
 Traces of chlorine The temperature at the base of the reaction zone was 60° C.

The pressure was 4 bars gauge.

4.38 kg/hr of liquid chlorine and 11.52 kg/hr of chloroform were introduced as starting materials.

The rate of recirculation was 0.16 m/sec.

In the separator 9 at the head of the reactor the gaseous and liquid phases were obtained at the following rates of flow and having the following compositions:
(i) Gaseous phase: 2.7 kg/hr of a mixture consisting of:
 HCl: 82.95%
 $Cl_2$: 1.71%
 $CCl_4 + CHCl_3$: 15.34%
(ii) Liquid phase: 13.29 kg/hr of a mixture consisting of:
 $CCl_4$: 69% by weight
 $CHCl_3$: 31% by weight The rate of conversion of the chlorine was 99%.
The rate of conversion of $CHCl_3$ into $CCl_4$ was 64%.

EXAMPLE 2

(1) The apparatus was as in Example 1, but with the following characteristics:
(i) Size of the cylindrical, principal reaction zone 1:
 (a) length: 6000 mm
 (b) internal diameter: 600 mm
(ii) Photochemical initiation:
 (a) 7 UV emitters 17 arrayed at each end of the reactor. Arc length of each emitter: 1500 mm. Diameter: 56.8 mm. Power: 3 kW each.
(iii) Separate inlets 4 and 5 for the reagents at the base of the reactor;

(iv) Liquid phase outlet via line 11 ⎫ at the head of
(v) Gaseous phase outlet via line 10 ⎭ the apparatus;

(vi) Cooling with water (tube exchanger 12).

(2) Within the loop 2 was circulated a mixture comprising (approximately) by weight:
 $Cl_2$: traces
 HCl: 1%
 $CH_3Cl$: 9%
 $CH_2Cl_2$: 40%
 $CHCl_3$: 40%
 $CHCl_4$: 10%

The temperature at the base of the reaction zone was 44° C.

The pressure was 4.1 bars gauge.

At the base of the reactor were introduced:
2985 kg/hr of liquid chlorine (line 4)
2928 kg/hr of $CH_3Cl$ (line 5)
934 kg/hr of $CH_2Cl_2$ (line 5)

The rate of recirculation was 0.42 m/sec.

In the separator 9 at the head of the reactor the gaseous and liquid phases were obtained at the following rates of flow and having the following compositions:
(i) Gaseous phase: 4160 kg/hr of a mixture consisting (by weight) of:
 $Cl_2$: traces
 HCl: 36%
 $CH_3Cl$: 33.5%
 $CH_2Cl_2$: 20%
 $CHCl_3$: 9%
 $CCl_4$: 1.5%
(ii) Liquid phase: 2687 kg/hr of the mixture indicated above (circulating mixture).

Rate of conversion of the chlorine: 99.8%

Total production per hour: 2751 kg/hr with a weight distribution of 35% $CH_2Cl_2$, 54% $CHCl_3$ and 11% $CCl_4$.

EXAMPLE 3

(1) The apparatus was also as in the FIGURE of Drawing and had the following characteristics:
(i) Dimensions of the cylindrical, principal reaction zone:
 (a) length: 1400 mm
 (b) internal diameter: 25 mm
(ii) Chemical initiation: continuous introduction by metering pump via line 18;
(iii) Separate inlets 4 and 5 for the reagents at the base of the reactor;
(iv) Liquid phase outlet via line 16 downstream of the heat exchanger 12 and upstream of the points of introduction of the reagents;
(v) Gaseous phase outlet via line 10;
(vi) Cooling with water, tube exchanger 12;
(vii) Total volume of the apparatus (reactor, exchanger, recirculation loop): 1.5 liters.

(2) Within the loop 2 was circulated a mixture comprising (approximately) by weight:
 $Cl_2$: traces
 HCl: about 5%
 $CH_3Cl$: 44%
 $CH_2Cl_2$: 35%
 $CHCl_3$: 5%
 $CCl_4$: 11%

The temperature at the base of the reaction zone was 45° C.

The pressure was 11 bars gauge.

At the base of the reactor were introduced:
(i) 1.6 g/hr of lauroyl peroxide in solution in $CCl_4$ (80 g/hr) (line 18);
(ii) 280 g/hr of gaseous chlorine (line 4);
(iii) 660 g/hr of $CH_3Cl$ (line 5).

The rate of recirculation was 1 m/sec.

The gaseous phase had the following rate of flow and composition:
(i) Rate of flow: 271 g/hr;

(ii) Composition by weight (approximately):
  Cl$_2$: traces
  CHCl$_3$: traces
  CCl$_4$: traces
  CH$_3$Cl: 54%
  HCl: 40%
  CH$_2$Cl$_2$: 5%

The liquid phase had a rate of flow of 749 g/hr.

This phase had the composition above indicated (circulating mixture).

The degree of conversion of the chlorine was greater than 99%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the continuous production of higher chloralkanes for at least one lesser chloroalkane, comprising (i) continuously introducing chlorine and said at least one lesser chloralkane into a stream of a liquid reaction medium which is continuously and essentially autogenously recirculating in a loop circuit which comprises an essentially vertically principle reaction zone, and a circulation loop (ii) continuously introducing said chlorine and lesser chloroalkane containing liquid reaction medium into the lower base portion of said vertical principal reaction zone, (iii) continuously chlorinating said at least one lesser chloralkane essentially in the liquid phase in said essentially vertical principal reaction zone, and (iv) continuously withdrawing from the circulation loop a portion of said stream of essentially autogenously recirculation reaction medium as the higher chloralkane product.

2. The process as defined by claim 1, further comprising (v) also continuously withdrawing gaseous effluent from said stream of essentially autogenously recirculating reaction medium.

3. The process as defined by claim 2, which comprises (ii) continuously chlorinating said at least one lesser chloroalkane in said essentially vertical principal reaction zone under temperature controlled conditions.

4. The process as defined by claim 3, which comprises the photochemically initiated continuous chlorination of said at least one lesser chloroalkane.

5. The process as defined by claim 4, wherein the amount of photochemical initiation comprises a luminance of from about 0.02 to 2 W/cm$^2$.

6. The process as defined by claim 3, which comprises the chemically initiated continuous free-radical chlorination of said at least one lesser chloroalkane.

7. The process as defined by claim 6, wherein the amount of chemical initiator ranges from about 10$^{-2}$ to 2.10$^{-6}$ mole thereof per mole of chlorine.

8. The process as defined by claim 3, hydrostatic pressure differentials existing within said stream of reaction medium, thus effecting said continuous and essentially autogenous recirculation thereof.

9. The process as defined by claim 8, wherein the rate of recirculation of said stream of reaction medium ranges from 0.05 to 1.5 meters/sec.

10. The process as defined by claim 9, said rate of recirculation ranging from 0.10 to 1 meter/sec.

11. The process as defined by claim 8, wherein the temperature at the principal reaction zone inlet ranges from about 20° to 120° C.

12. The process as defined by claim 11, said temperature ranging from about 30° to 90° C.

13. The process as defined by claim 11, wherein the chlorination is carried out under a pressure of from about 1 to 50 bars.

14. The process as defined by claim 13, said pressure ranging from about 2 to 30 bars.

15. The process as defined by claim 8, said stream of recirculating reaction medium comprising chlorine, HCl and chloroalkane.

16. The process as defined by claim 15, wherein the at least one lesser chloroalkane comprises methyl chloride, or admixture thereof with at least one other lesser chloromethane.

17. The process as defined by claim 15, wherein the at least one lesser chloroalkane comprises ethyl chloride, or admixture thereof with at least one other lesser chloroethane.

18. The process as defined by claim 8, wherein the molar ratio of the chlorine to the at least one lesser chloroalkane ranges from about 0.3/1 to 3/1.

19. The process as defined by claim 2, said gaseous effluent comprising chlorine, HCl and chloroalkane.

20. Apparatus for the continuous production of higher chloralkanes, comprising (1) a loop circuit including an essentially vertical principal reaction zone and a circulation loop, (2) means for continuously introducing chlorine and at least one lesser chloroalkane into said loop circuit, (3) means for temperature controlledly continuously chlorinating at least one lesser chloralkane in said essentially vertical principal reaction zone, (4) means for continuously withdrawing higher chloralkane product from said loop circuit, and (5) means for continuously withdrawing gaseous chlorination effluent from said loop circuit whereby a continuous and essentially autogenous recirculating stream of liquid reaction medium is established within said loop circuit.

21. The appartatus as defined by claim 20, said essentially vertical principal reaction zone comprising at least one photochemical emitter.

22. The apparatus as defined by claim 20, further comprising means for introducing a chemical initiator into said loop circuit.

23. The apparatus as defined by claim 20, wherein said essentially vertical principal reaction zone comprises a substantially cylindrical reactor.

24. The apparatus as defined by claim 23, said cylindrical reactor having a length/diameter ratio of from about 5 to 100.

25. The apparatus as defined by claim 24, said cylindrical reactor having a length of from about 0.1 to 15 meters.

26. The apparatus as defined by claim 23, said cylindrical reactor having a length/diameter ratio of from about 25 to 1000.

27. The apparatus as defined by claim 26, said cylindrical reactor having a length of from about 1 to 20 meters.

28. The apparatus as defined by claim 20 wherein hydrostatic prssure differences are established within the stream of autogenously recirculating liquid reaction medium.

29. The apparatus as defined by claim 20, further comprising a plurality of said loop circuits, arranged in parallel.

* * * * *